United States Patent
Shim et al.

(10) Patent No.: US 11,433,019 B2
(45) Date of Patent: Sep. 6, 2022

(54) GANODERMA LUCIDUM EXTRACT-PREPARING METHOD USING ECO-FRIENDLY EXTRACTION TECHNIQUE, GANODERMA LUCIDUM EXTRACT PREPARED THEREBY, AND ANTI-AGING COSMETIC COMPOSITION COMPRISING SAME EXTRACT

(71) Applicant: AMOREPACIFIC CORPORATION, Seoul (KR)

(72) Inventors: Jin Sup Shim, Yongin-si (KR); Eun Jung Lee, Yongin-si (KR); Nok Hyun Park, Yongin-si (KR); So Woong Choi, Yongin-si (KR); Yong Jin Kim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 86 days.

(21) Appl. No.: 16/651,966

(22) PCT Filed: Sep. 20, 2018

(86) PCT No.: PCT/KR2018/011126
§ 371 (c)(1),
(2) Date: Mar. 27, 2020

(87) PCT Pub. No.: WO2019/066381
PCT Pub. Date: Apr. 4, 2019

(65) Prior Publication Data
US 2020/0253859 A1    Aug. 13, 2020

(30) Foreign Application Priority Data

Sep. 28, 2017 (KR) .................. 10-2017-0126385

(51) Int. Cl.
A61K 36/00 (2006.01)
A61K 8/9728 (2017.01)
A61K 8/31 (2006.01)
A61K 8/73 (2006.01)
A61Q 19/08 (2006.01)

(52) U.S. Cl.
CPC .............. *A61K 8/9728* (2017.08); *A61K 8/31* (2013.01); *A61K 8/738* (2013.01); *A61Q 19/08* (2013.01); *A61K 2800/57* (2013.01); *A61K 2800/59* (2013.01); *A61K 2800/82* (2013.01)

(58) Field of Classification Search
CPC ........................... A61K 2800/82; A61K 8/738
See application file for complete search history.

(56) References Cited

U.S. PATENT DOCUMENTS

| | | |
|---|---|---|
| 5,780,096 A | 7/1998 | Tanaka |
| 5,780,097 A | 7/1998 | Tanaka |
| 2016/0184373 A1 | 6/2016 | Zhang et al. |

FOREIGN PATENT DOCUMENTS

| | | | |
|---|---|---|---|
| CN | 1765374 A | * | 5/2006 |
| CN | 100364554 C | * | 1/2008 |
| CN | 101966141 A | | 2/2011 |
| CN | 104306410 A | | 1/2015 |
| CN | 104922167 A | * | 9/2015 |
| GB | 2 265 073 A | | 9/1993 |
| GB | 2 265 074 A | | 9/1993 |
| JP | 58109424 A | * | 6/1983 |
| KR | 1993-0007475 B1 | | 8/1993 |
| KR | 1993-0007476 B1 | | 8/1993 |
| KR | 10-0847225 B1 | | 7/2008 |

OTHER PUBLICATIONS

International Search Report for PCT/KR2018/011126 filed Jan. 7, 2019 [PCT/ISA/210].
Written Opinion for PCT/KR2018/011126 filed Jan. 7, 2019 [PCT/ISA/237].
Chinese Patent Office, Communication dated Jun. 28, 2022 in copending Chinese Application No. 201880062866.1 with full English translation.

* cited by examiner

*Primary Examiner* — Qiuwen Mi
(74) *Attorney, Agent, or Firm* — Sughrue Mion, PLLC

(57) ABSTRACT

A method for preparing *Ganoderma lucidum* extract using an eco-friendly extraction technique is disclosed. A *Ganoderma lucidum* extract prepared thereby and a cosmetic composition containing the extract, and their uses are disclosed. The extraction technique use an aqueous cyclodextrin solution alone or in combination with ultrasonic extraction to afford a *Ganoderma lucidum* extract containing a high concentration of the effective ingredient triterpenoid.

7 Claims, 2 Drawing Sheets

[FIG. 1]
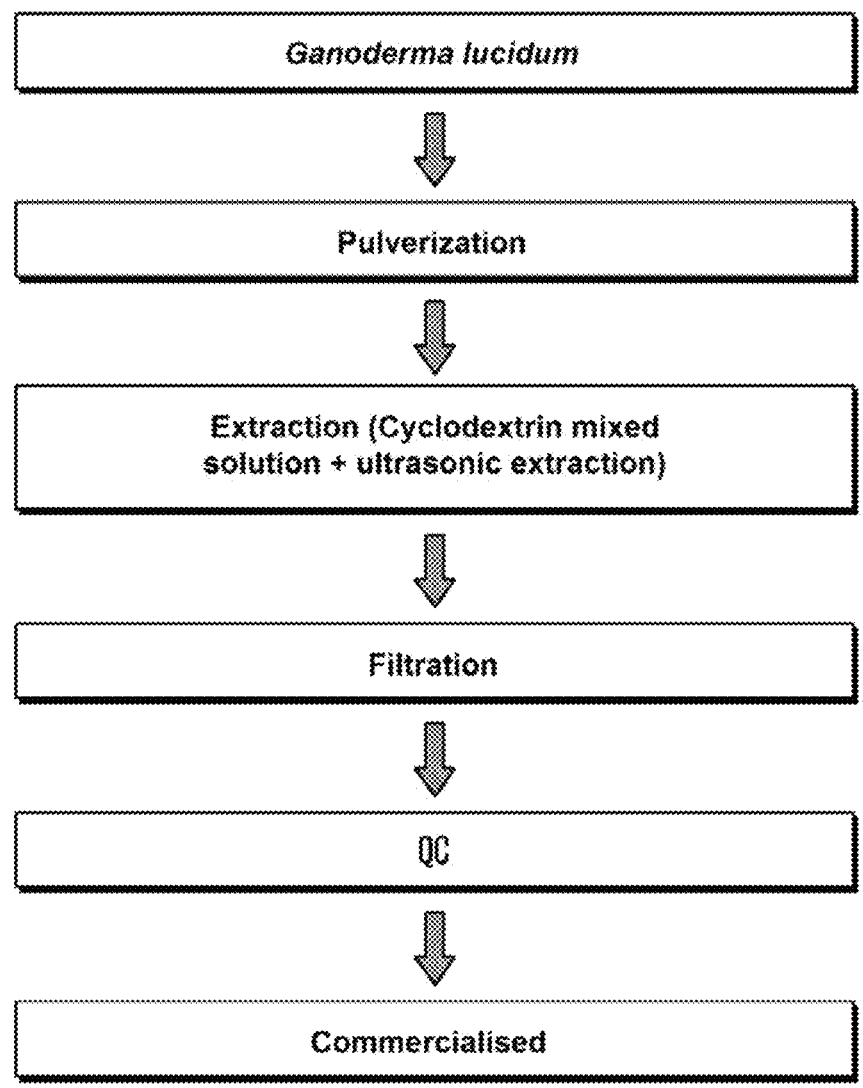

[FIG. 2]
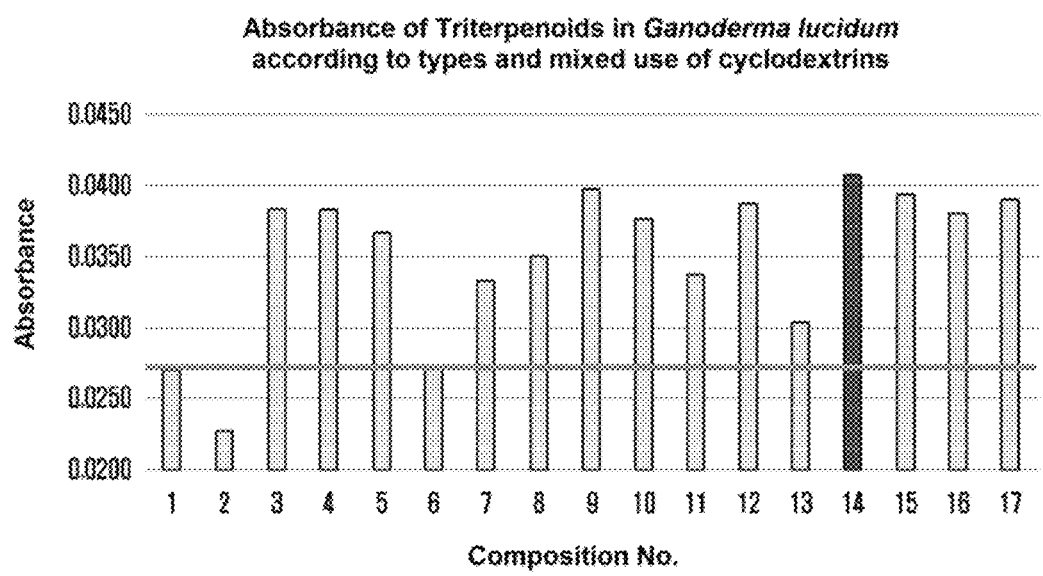

GANODERMA LUCIDUM EXTRACT-PREPARING METHOD USING ECO-FRIENDLY EXTRACTION TECHNIQUE, GANODERMA LUCIDUM EXTRACT PREPARED THEREBY, AND ANTI-AGING COSMETIC COMPOSITION COMPRISING SAME EXTRACT

CROSS REFERENCE TO RELATED APPLICATIONS

This application is a National Stage of International Application No. PCT/KR2018/011126 filed Sep. 20, 2018, claiming priority based on Korean Patent Application No. 10-2017-0126385 filed Sep. 28, 2017.

TECHNICAL FIELD

The present disclosure relates to a method for preparing a *Ganoderma lucidum* extract using an eco-friendly extraction technique, a Ganoderma lucidum extract prepared thereby, and a cosmetic composition containing the extract. More particularly, it relates to a method for preparing a *Ganoderma lucidum* extract, which utilizes an extraction technique using an aqueous cyclodextrin solution or an extraction technique using an aqueous cyclodextrin solution in combination with ultrasonic extraction to afford a *Ganoderma lucidum* extract containing a high concentration of the effective component triterpenoid, thereby increasing anti-aging effects such as suppression of MMP-1 activity and inhibition of collagen degradation, a *Ganoderma lucidum* extract prepared thereby, and a cosmetic composition containing the extract. In addition, the present disclosure relates to the use of the cosmetic composition containing a Ganoderma lucidum extract in reducing skin wrinkles and increasing skin elasticity, and a method for reducing skin wrinkles and a method for increasing skin elasticity using the composition.

BACKGROUND ART

*Ganoderma lucidum* is a mushroom belonging to the family Ganodermataceae in the order of Aphyllophorales in the phylum of *Basidiomycota*, has a shape of a kidney, a semi-circle or a fan, and is 5 to 20 cm in diameter. It has ring-shaped grooves on the surface of the brown cap and fine wrinkles in the radial direction. It is widely distributed in the temperate regions of the northern hemisphere, and is a year-old mushroom that grows mainly at the root base of deciduous trees or stumps of dead trees from early summer to autumn.

*Ganoderma lucidum*, also referred to as *bullocho* (elixir grass) or perennial mushroom, has been used as a traditional medicinal herb because of its efficacy in stabilizing the mind and body, replenishing energy and blood, calming cough, and the like, and has been found to be effective in hypertension, hypercholesterolemia, hepatitis, gastritis, diabetes, bronchitis, cardiovascular diseases, and the like. Recently, studies related to anticancer treatment have been actively conducted. In addition, the fruit body extract of *Ganoderma lucidum* is being used for health functional foods, and attempts to utilize Ganoderma lucidum as an anti-aging cosmetic material have been made.

It is known that the chemical components of Ganoderma lucidum include ganoderan A•B•C, ganoderic acids, ganoderol A•B, lucidenic acids, ergosterol, mannitol, hemicellulose, β-D-glucan, mannoglucan, peptidoglucan, coumarin, 5'-GMP, 5'-ADP, and the like.

Among them, β-D-glucan, which a polysaccharide, is a major bioactive component that is essentially contained in health functional foods containing the fruit body extract of *Ganoderma lucidum*. Triterpenoids of ganoderic acid and lucidenic acid have also been found to be bioactive components useful for pharmacological actions and immune functions. In particular, ganoderic acids are known to have pharmacological activity in a wide range of diseases, including cytotoxicity of liver cancer cells.

As the extraction methods for preparing a *Ganoderma lucidum* extract, a method using hot water and a method using organic solvents are generally known.

The extraction method using hot water is mainly used to easily extract polysaccharide components from *Ganoderma lucidum*, or to use the *Ganoderma lucidum* extract as a functional component in general foods. However, it is difficult to obtain a *Ganoderma lucidum* extract containing a high concentration of anti-aging components such as triterpenoids by the simple hot water extraction method currently being carried out.

The extraction method using organic solvents is preferred when pharmacologically active components are to be obtained from *Ganoderma lucidum*. The purpose of this extraction method is for easily separating the active ingredients which are not water-soluble using an aqueous organic solvent such as ethanol, methanol, or lower alcohol, or for extracting the active ingredients at high concentrations. However, there may be a problem in terms of safety because the organic solvent may itself be toxic, and there is a disadvantage that because foreign substances may have been mixed and extracted, an additional purification process for removing them should be carried.

Therefore, in the utilization of the anti-aging component of *Ganoderma lucidum*, it is necessary to develop a method that can extract, in a high concentration, active ingredients contained in *Ganoderma lucidum*, while being safe for the human body because of not using an organic solvent.

In one of these methods, the present disclosure is intended to propose a method for extracting a high concentration of the triterpenoid component from *Ganoderma lucidum* using the inclusion ability of cyclodextrin.

Cyclodextrins are natural biomaterials and are ring-shaped maltooligosaccharides bound circularly by a-1,4-glucoside bonds. Depending on the degree of polymerization of D-glucose, it can be classified into α-cyclodextrin (6) and β-cyclodextrin (7), γ-cyclodextrin (8), and the like. In addition, cyclodextrins have a hydrophobic cavity inside the doughnut structure, and have a unique characteristic of forming a clathrate compound by inserting various compounds into the inner cavity, and cyclodextrins are known to be non-toxic and very safe for the living body since the constitutional units is glucose.

Extraction methods using cyclodextrin have been used in the preparation of shiitake mushroom powder extract disclosed in U.S. Pat. No. 5,780,097, in the preparation of chlorella extract disclosed in U.S Pat. No. 5,780,096, in the isoflavone extraction from plants disclosed in Korean Patent Application No. 10-2003-0074765, and the like.

However, there has not been reported any case where the inclusion ability of cyclodextrin is applied in the preparation of a *Ganoderma lucidum* extract in order to use the triterpenoid component of *Ganoderma lucidum* for anti-aging cosmetics. In addition, a method for further increasing the extraction efficiency of the active ingredient during the extraction of the active ingredient using cyclodextrin has not been further suggested.

PRIOR ART DOCUMENTS

Patent Documents (Patent Document 1) Korean Application No. 10-2003-0074765 (published on Apr. 29, 2005)
(Patent Document 2) U.S. Pat. No. 5,780,097 (published on Jul. 14, 1998)
(Patent Document 3) U.S. Pat. No. 5,780,096 (published on Jul. 14, 1998)

DETAILED DESCRIPTION OF THE INVENTION

Technical Problem

In the prior art, in order to obtain *Ganoderma lucidum* extracts, a simple hot water extraction method has been used, or organic solvents such as ethanol, methanol, ethyl acetate or the like have been used. However, the simple hot water extraction method gives a low yield of the active ingredient. The organic solvent extraction method gives a higher yield compared to the hot water extraction, but after extraction, it involves a complicated process, such as removing the organic solvent or the like, and due to the toxicity of the organic solvent itself, there is a problem that does not satisfy the safety and eco-friendly elements when applied to the human body.

An object of the present disclosure is to provide a method for preparing a *Ganoderma lucidum* extract, which can contain an anti-aging active ingredient in a high concentration, while being safe to human body and being not complicated in processes since organic solvents are not used.

Another object of the present disclosure is to provide a *Ganoderma lucidum* extract prepared thereby and an anti-aging cosmetic composition containing the extract.

Technical Solution

In order to achieve the above objects, the present disclosure provides a method for preparing a *Ganoderma lucidum* extract containing a high concentration of triterpenoids using an eco-friendly extraction technique, a *Ganoderma lucidum* extract prepared thereby, and an anti-aging cosmetic composition containing the extract as an active ingredient. Specifically, the present disclosure provides a method for preparing a Ganoderma lucidum extract containing a high concentration of triterpenoids by an extraction method using an aqueous cyclodextrin solution, or an extraction technique using an aqueous cyclodextrin solution in combination with ultrasonic extraction, and a cosmetic composition containing the *Ganoderma lucidum* extract prepared by the above method.

More specifically, the method for preparing a *Ganoderma lucidum* extract of the present disclosure is carried out such that *Ganoderma lucidum* is added to an aqueous solution of cyclodextrin, cyclodextrin derivatives, or cyclodextrin polymers, thereby conjugating the triterpenoid component of *Ganoderma lucidum* with the cyclodextrin, cyclodextrin derivatives, or cyclodextrin polymers and extracting the same. In addition, the present disclosure provides a method for extracting the triterpenoid component of *Ganoderma lucidum* in a high concentration to the maximum by optimizing the type and mixing ratio of the cyclodextrin constituting the aqueous cyclodextrin solution. Moreover, the present disclosure provides a method for further increasing the extraction yield of triterpenoids by combining an ultrasonic treatment with the extraction process using the aqueous cyclodextrin solution.

Furthermore, the present disclosure provides the use of the cosmetic composition containing a *Ganoderma lucidum* extract containing a high concentration of triterpenoids in reducing skin wrinkles and increasing skin elasticity, and a method for reducing skin wrinkles and a method for increasing skin elasticity using the composition.

Advantageous Effects

The method for extracting triterpenoids of *Ganoderma lucidum* according to the present disclosure is simple in the processes compared to a conventional organic solvent extraction method, and thus has the effect of significantly reducing the cost of separation-purification, and has an advantage of being safe and eco-friendly because of reducing the use of organic solvents, which can be harmful to the environment and human body.

In addition, by establishing the most suitable type, mixing ratio, and processing conditions of cyclodextrin in the extraction process using an aqueous cyclodextrin solution, anti-aging components of *Ganoderma lucidum* can be extracted in a high efficiency even with low costs, and by combining ultrasonic extraction thereto, higher efficiency can be provided.

The *Ganoderma lucidum* extract prepared by the method for preparing a *Ganoderma lucidum* extract according to the present disclosure contains a high concentration of the active ingredients of *Ganoderma lucidum*, and is not toxic and safe to the human body, and thus can be easily utilized as a material for cosmetics and health functional foods.

Further, the anti-aging cosmetic composition containing the *Ganoderma lucidum* extract contains a high concentration of triterpenoids, thereby providing excellent effects in suppressing MMP-1 and inhibiting collagenase, and thus can be used in cosmetics for reducing skin wrinkles and increasing skin elasticity. Thereby, products which is safe while having high performance can be provided to consumers.

BRIEF DESCRIPTION OF THE DRAWINGS

FIG. 1 shows the preparation process of the *Ganoderma lucidum* extract containing a high concentration of triterpenoids according to the present disclosure.

FIG. 2 is a graph comparing the absorption of triterpenoids contained in *Ganoderma lucidum* extracts after preparing the *Ganoderma lucidum* extracts using aqueous cyclodextrin solutions according to various mixing ratios of α-CD, β-CD, and γ-CD.

DETAILED DESCRIPTION OF THE EMBODIMENTS

One embodiment of the present disclosure relates to a method for preparing a *Ganoderma lucidum* extract containing triterpenoids using an aqueous cyclodextrin solution, comprising the step of adding *Ganoderma lucidum* containing the triterpenoid component to an aqueous cyclodextrin solution to form a conjugate of the cyclodextrin and the triterpenoid component of the *Ganoderma lucidum*.

Another embodiment of the present disclosure relates to a method for preparing a *Ganoderma lucidum* extract containing triterpenoids, comprising the step of forming the conjugate by adding an ultrasonic treatment in the step of forming a conjugate of the cyclodextrin and the triterpenoid component of the *Ganoderma lucidum*.

Further, the present disclosure relates to a *Ganoderma lucidum* extract containing triterpenoids prepared by the method for preparing an extract using an aqueous cyclodextrin solution.

The method for preparing a *Ganoderma lucidum* extract according to the present disclosure is characterized in that the conjugate of the cyclodextrin and the triterpenoid is formed by adding *Ganoderma lucidum* containing the triterpenoid component to an aqueous cyclodextrin solution.

In addition, the method for preparing a *Ganoderma lucidum* extract according to the present disclosure can further increase the formation efficiency of the conjugate by adding an aqueous cyclodextrin solution to *Ganoderma lucidum* and extracting the same in combination with ultrasonic treatment.

In the extraction of the active ingredient of *Ganoderma lucidum*, the present disclosure has a feature of using an aqueous cyclodextrin solution instead of an organic solvent. Preferably, water at room temperature or hot water containing an appropriate concentration of cyclodextrin may be used.

As the *Ganoderma lucidum* containing the triterpenoid component, *Ganoderma lucidum*, *Ganoderma sinensis*, *Ganoderma atrum*, *Ganoderma neojaponicum*, and the like may be used, but is not limited thereto, and lingzhi mushroom, commercially available at herbal shops, can be used as raw materials.

The cyclodextrin used in the aqueous cyclodextrin solution according to the present disclosure may be α-cyclodextrin, β-cyclodextrin, or γ-cyclodextrin, and may be a cyclodextrin derivative or a polymer of cyclodextrin. It may also be a mixture of two or more selected from the above-listed cyclodextrins, cyclodextrin derivatives, and cyclodextrin polymers, and the concentration of the triterpenoid component contained in the *Ganoderma lucidum* extract may vary depending on the combination and mixing ratio thereof.

As the cyclodextrin in the aqueous cyclodextrin solution, α-cyclodextrin, β-cyclodextrin, or γ-cyclodextrin may be used, and (2-Hydroxypropyl)-α-cyclodextrin (molecular weight of about 1180, CAS 128446-33-3), (2-Hydroxypropyl)-β-cyclodextrin (molecular weight of about 1400, CAS 128446-35-5), (2-Hydroxypropyl)-γ-cyclodextrin (molecular weight of about 1580, CAS 128446-34-4), methyl-β-cyclodextrin (molecular weight of about 1310, CAS 128446-36-6) or the like may be used. In addition, one or more selected from the group consisting of polymers of the cyclodextrins, polymers of the cyclodextrin derivatives, or polymer of the cyclodextrins and the cyclodextrin derivatives may be used.

In the aqueous cyclodextrin solution, when α-cyclodextrin, β-cyclodextrin, γ-cyclodextrin, hydroxypropyl α-cyclodextrin, hydroxypropyl β-cyclodextrin, hydroxypropyl γ-cyclodextrin, or methyl β-cyclodextrin is used alone, it is not preferable to use α-cyclodextrin alone, but it is preferable to use β-cyclodextrin, γ-cyclodextrin, hydroxypropyl β-cyclodextrin, hydroxypropyl γ-cyclodextrin, or methyl β-cyclodextrin.

Further, in the aqueous cyclodextrin solution, it is preferable to use a mixture of β-cyclodextrin and γ-cyclodextrin in a weight ratio of 1:1 rather than using α-cyclodextrin, β-cyclodextrin, or γ-cyclodextrin alone.

In addition, in the aqueous cyclodextrin solution, when three types of α-cyclodextrin, β-cyclodextrin, and γ-cyclodextrin are mixed, the mixing ratio of α-cyclodextrin, β-cyclodextrin, and γ-cyclodextrin is preferably in a weight ratio of 1:1 to 2:0.5 to 2, and it is most preferable that the mixing ratio of α-cyclodextrin, β-cyclodextrin and γ-cyclodextrin is in a weight ratio of 1:1:1. However, all types of cyclodextrins mentioned above may be used, and the materials used in the preparation method of the present disclosure are not limited thereto.

In the step of forming a conjugate of the cyclodextrin and the triterpenoid of the *Ganoderma lucidum*, the concentration of cyclodextrin in the aqueous cyclodextrin solution is preferably 0.01 to 30% (weight/volume), more preferably 0.5 to 5% (weight/volume), relative to the total volume of the aqueous solution. If the concentration of the aqueous cyclodextrin solution is less than 0.01% (weight/volume), the binding rate may be significantly reduced, which may cause in a reduction in extraction efficiency, and if the concentration exceeds 30% (weight/volume), the extraction efficiency may no longer increase and become saturated.

The extraction time for forming the conjugate is preferably 10 minutes to 24 hours. If it is less than 10 minutes, the extraction efficiency may be reduced, and even if the extraction time exceeds 24 hours, the extraction efficiency may not increase in proportion to time and may become almost saturated, and thus, it is preferable not to exceed 24 hours in terms of cost. The more preferable extraction time for forming the conjugate is 30 minutes to 240 minutes. In particular, the extraction temperature for forming the conjugate is preferably 15° C. to 100° C.

When an ultrasonic extraction is to be performed in combination during the formation process of the conjugate, the ultrasonic (20 kHz to 25 MHz) extraction is preferably performed at 15° C. to 35° C. for 10 minutes to 120 minutes, and most preferably at 15° C. to 35° C. for 15 minutes to 60 minutes.

The present disclosure relates to a cosmetic composition containing a *Ganoderma lucidum* extract containing a high concentration of triterpenoids, as an active ingredient, prepared by the extraction method using the aqueous cyclodextrin solution.

The cosmetic composition according to the present disclosure may contain the *Ganoderma lucidum* extract containing triterpenoids in an amount of 0.0001% by weight to 30% by weight, preferably 0.001% by weight to 10% by weight, based on the total weight of the composition, and most preferably 0.01% by weight to 1% by weight.

The present disclosure relates to the use of the cosmetic composition containing the *Ganoderma lucidum* extract containing triterpenoids in reducing skin wrinkles and increasing skin elasticity, and a method for reducing skin wrinkles and a method for increasing skin elasticity using the composition.

The cosmetic composition according to the present disclosure contains the triterpenoid component in a high concentration, thereby increasing anti-aging effects such as suppression of MMP-1 activity and inhibition of collagenase, and accordingly, it can be used to reduce skin wrinkles and increase skin elasticity.

The cosmetic composition according to the present disclosure may be formulated into softening cosmetic water, astringent cosmetic water, nourishing cosmetic water, nourishing cream, massage cream, essence, eye cream, eye essence, cleansing cream, cleansing foam, cleansing water, facial pack, powder, body lotion, shampoo, conditioner, body wash, tooth paste or mouth wash, and used in cosmetics.

MODE FOR CARRYING OUT THE INVENTION

Hereinafter, the present disclosure will be described by way of Example and Test Examples. However, these Examples and Test Examples are given for illustrative purposes only to help understanding of the present disclosure, and the scope of the present disclosure is not limited by these examples.

TEST EXAMPLE 1

Extraction Efficiency of Triterpenoids in Ganoderma lucidum Using Cyclodextrin

In this test, the extraction using an aqueous cyclodextrin solution was carried out as follows: To 200 ml of an aqueous solution, which was prepared by dissolving α-cyclodextrin (α-CD), β-cyclodextrin (β-CD), hydroxypropyl beta cyclodextrin (HP-β-CD), or γ-cyclodextrin (γ-CD) at a concentration of 1% (weight/volume) in water was added 10 g of pulverized Ganoderma lucidum, and the mixture was extracted at 95° C. for 60 minutes. Thereby, extracts of Examples 1 to 4 were obtained, and the extracts were used for analysis.

The extraction using water (distilled water) as a control was performed in the same order except that the process of dissolving cyclodextrin in water was omitted in the extraction process using the aqueous cyclodextrin solution. 10 g of Ganoderma lucidum was suspended in 200 ml of water, and then extracted under the same reaction conditions and time as the extraction process using the aqueous cyclodextrin solution to obtain an extract of Comparative Example 1, which was used for analysis.

In addition, the aqueous cyclodextrin solution-ultrasonic extraction used in this test utilizes the extraction using the aqueous cyclodextrin solution in combination with ultrasonic extraction, and the ultrasonic extraction was carried out using an ultrasonic extractor (Branson Ultrasonics Sonifier™ S-450D) at room temperature (20° C.) at 60 KHz for 15 minutes.

The obtained extracts were filtered through a 0.45 μm filter, and then used as HPLC samples and analyzed by HPLC-PDA system. HPLC analysis was carried out using Waters Alliance system (model 2965) and photodiode array (PDA, model 2996). Luna® 5 μm C18 (2) (100 Å, LC column 250×4.6 mm) was used as analytical columns, and water and acetonitrile were used as mobile phase.

The results are shown in Table 1.

TABLE 1

| | | Aqueous Cyclodextrin Solution Extraction | | Aqueous Cyclodextrin Solution * Ultrasonic Assisted extraction | |
| --- | --- | --- | --- | --- | --- |
| | | Area | Relative to Control | Area | Relative to Control |
| Comparative Example 1 | Water (Distilled water) | 318486 | 100% | 281655 | 100% |
| Example 1 | 1% α-CD Aqueous solution | 290482 | 94% | 321539 | 114% |
| Example 2 | 1% β-CD Aqueous solution | 416196 | 131% | 466576 | 166% |
| Example 3 | 1% HP-β-CD Aqueous solution | 425589 | 134% | 410915 | 146% |
| Example 4 | 1% γ-CD Aqueous solution | 438854 | 138% | 456253 | 162% |

As shown in Table 1, when the extraction method using the aqueous cyclodextrin solution according to the present disclosure was used, it was confirmed that the Ganoderma lucidum extract containing a high concentration of triterpenoids, which is an active ingredient of Ganoderma lucidum, was obtained. In the case of Examples 2 to 4 in which the extraction was carried out using 1% β-CD aqueous solution, 1% HP-β-CD aqueous solution, or 1% γ-CD aqueous solution, the concentration of triterpenoids (ganoderic acid, etc.) extracted from the Ganoderma lucidum was increased by about 30 to 40% compared to when using the conventional water extraction method. However, in the case of Example 1 in which the extraction was carried out using 1% α-CD aqueous solution, the concentration of triterpenoids was rather decreased compared to Comparative Example 1 using the simple water extraction.

In addition, in the case of the extraction technique in which the extraction method using the aqueous cyclodextrin solution according to the present disclosure was combined with ultrasonic extraction, the concentration of triterpenoids extracted from Ganoderma lucidum was increased in all cases of 1% α-CD aqueous solution, 1% β-CD aqueous solution, 1% HP-β-CD aqueous solution, and 1% γ-CD aqueous solution (Examples 1 to 4 in combination with ultrasonic extraction) compared to the control group (Comparative Example 1 in combination with ultrasonic extraction). In particular, when the extraction using 1% β-CD aqueous solution or 1% γ-CD aqueous solution was combined with ultrasonic extraction, the extraction concentration of triterpenoids was increased by 60% or more compared to the control group, thereby showing excellent extraction efficiency.

TEST EXAMPLE 2

Extraction Efficiency of Triterpenoid in Ganoderma lucidum According to Types and Mixed Use of Cyclodextrins In this test, the extraction method using the aqueous cyclodextrin solution was performed in combination with ultrasonic extraction. As the aqueous cyclodextrin solution, an aqueous solution prepared by diluting cyclodextrin to 1% (weight/volume) in water was used, and in particular, the cyclodextrin was one selected from the group consisting of α-CD, β-CD, or γ-CD, or a mixture of two or more thereof. Thereafter, 10 g of pulverized Ganoderma lucidum was added to 200 ml of the aqueous solution, followed by ultrasonic extraction to obtain an extract, which was filtered and used for analysis. The ultrasonic extraction was performed at room temperature (20° C.) at 40 KHz for 30 minutes using an ultrasonic extractor (Branson Ultrasonics CPX952838R).

The extraction using water (distilled water) as a control was performed in the same order except that the process of dissolving cyclodextrin in water was omitted in the extraction process using the aqueous cyclodextrin solution. 10 g of Ganoderma lucidum was suspended in 200 ml of water, and then extracted under the same reaction conditions and time as the extraction process using the aqueous cyclodextrin solution to obtain an extract, which was used for analysis.

The extracts were allowed to react with 5% valine-acetic acid and perchloric acid and then analyzed by measuring the absorbance of triterpenoids at 550 nm using Biotek™ Synergy 2.

The results are shown in Table 2 and FIG. 2.

TABLE 2

| Composition No. | | Cyclodextrin 1% Mixing ratio | | | Absorbance |
|---|---|---|---|---|---|
| | | α-CD | β-CD | γ-CD | |
| 1 | Comparative Example 1 | 0.0% | 0.0% | 0.0% | 0.0270 |
| 2 | Example 1 | 100.0% | 0.0% | 0.0% | 0.0227 |
| 3 | Example 2 | 0.0% | 100.0% | 0.0% | 0.0383 |
| 4 | Example 4 | 0.0% | 0.0% | 100.0% | 0.0383 |
| 5 | Example 5 | 66.7% | 0.0% | 33.3% | 0.0367 |
| 6 | Example 6 | 50.0% | 0.0% | 50.0% | 0.0273 |
| 7 | Example 7 | 33.3% | 0.0% | 66.7% | 0.0333 |
| 8 | Example 8 | 0.0% | 66.7% | 33.3% | 0.0350 |
| 9 | Example 9 | 0.0% | 50.0% | 50.0% | 0.0397 |
| 10 | Example 10 | 0.0% | 33.3% | 66.7% | 0.0377 |
| 11 | Example 11 | 50.0% | 25.0% | 25.0% | 0.0337 |
| 12 | Example 12 | 40.0% | 40.0% | 20.0% | 0.0387 |
| 13 | Example 13 | 40.0% | 20.0% | 40.0% | 0.0303 |
| 14 | Example 14 | 33.3% | 33.3% | 33.3% | 0.0407 |
| 15 | Example 15 | 25.0% | 50.0% | 25.0% | 0.0393 |
| 16 | Example 16 | 25.0% | 25.0% | 50.0% | 0.0380 |
| 17 | Example 17 | 20.0% | 40.0% | 40.0% | 0.0390 |

As shown in Table 2 and FIG. 2, when the extraction was carried out using 1% aqueous cyclodextrin solution, it was confirmed that the absorbance was found to be high in all Examples except for using α-CD alone compared to Comparative Example 1 using the simple water extraction method. That is, in the case of Example 2 and Examples 4 to 17, the concentration of triterpenoids extracted from Ganoderma lucidum was higher than that of Comparative Example 1, and accordingly, high extraction efficiency was confirmed.

In addition, in the 1% aqueous cyclodextrin solution, a higher absorbance was observed when two types of β-CD and γ-CD were mixed at a mixing ratio of 1:1 or when three types of α-CD, β-CD, and γ-CD were mixed at a predetermined ratio, compared to when α-CD, β-CD, or γ-CD was used alone, resulting in a higher extraction concentration of triterpenoids from Ganoderma lucidum. In particular, in the case of in which three types of α-CD, β-CD, and γ-CD were mixed and used, a higher absorbance was observed when the mixture of α-CD, β-CD, and γ-CD was used in a mixing ratio of 1:1 to 2:0.5 to 2 compared to when they were used alone, and the absorbance was found to be the highest when α-CD, β-CD, and γ-CD were mixed and used in a mixing ratio of 1:1:1, confirming that triterpenoids could be extracted at the highest concentration.

TEST EXAMPLE 3

MMP-1 Inhibitory Effect of Ganoderma lucidum Extracts Extracted with Aqueous Cyclodextrin Solution In order to confirm the inhibitory effect of Ganoderma lucidum extracts extracted with the aqueous cyclodextrin solution according to the present disclosure on matrix metalloprotease-1 (MMP-1) expression increased by ultraviolet rays, fibroblasts cells (HS68) were seeded at a concentration of $0.75*10^5$ in each well of a 12 well plate and made to be a starvation state for 24 hours, then washed with phosphate buffered saline and irradiated with UV (30 mJ). Subsequently, as a positive control, 1, 10, and 50 ppm of Ganoderma lucidum extracts extracted with 5 μM of retinoic Acid (RA) and an aqueous cyclodextrin solution were treated twice for 48 hours, and the amount of free MMP-1 in the media was measured using a kit (Amersham, RPN2610).

The Ganoderma lucidum extracts were those extracted by using the 1% β-CD aqueous cyclodextrin solution in combination with the ultrasonic extraction, and the data values were corrected with the control that does not contain a test substance. The results are shown in Table 3.

TABLE 3

| | Concentration | Extracellular MMP-1 (% of control) |
|---|---|---|
| Control | | 0% |
| Positive control (Retinoic acid) | 5 μM | 66.2% |
| Ganoderma lucidum extract extracted using water (distilled water) | 50 ppm | 37.1% |
| Ganoderma lucidum extracts extracted using aqueous cyclodextrin solution (1% β-CD aqueous solution * Ultrasonic Assisted extraction) | 1 ppm | 26.5% |
| | 10 ppm | 47.1% |
| | 50 ppm | 51.3% |

As shown in Table 3, the Ganoderma lucidum extracts extracted using the aqueous cyclodextrin solution according to the present disclosure inhibited the expression of MMP-1 with increasing concentration. In addition, the Ganoderma lucidum extracts showed excellent MMP-1 expression inhibitory effect compared to the Ganoderma lucidum extract extracted with water without using the aqueous cyclodextrin solution.

TEST EXAMPLE 4

Collagenase Inhibitory Effect of Ganoderma lucidum Extracts Extracted with Aqueous Cyclodextrin Solution The inhibitory ability of Ganoderma lucidum extracts extracted with the aqueous cyclodextrin solution according to the present disclosure on collagenase production was measured in comparison with retinoic acid. Human fibroblasts were added at 5,000 cells/well in a 96-well microtiter plate containing Dulbecco's Modified Eagle's Media (DMEM) medium containing 2.5% fetal bovine serum and incubated in an incubator (5% $CO_2$, 37° C.) until the growth reached 70 to 80%. Then, the Ganoderma lucidum extracts, which were extracted using the 1% β-CD aqueous cyclodextrin solution in combination with ultrasonic extraction, were treated with the cells at a concentration of 100 μg/ml for 24 hours, and then the cell culture solution was collected.

Then, the degree of collagenase production in the thus-collected cell culture solution was measured using a commercially available collagenase measuring instrument (GE Healthcare Life Sciences). First, the collected cell culture solution was placed in a 96-well plate uniformly coated with primary collagenase antibodies, and the antigen-antibody reaction was performed in a constant-temperature bath for 3 hours. After 3 hours, chromophore-conjugated secondary collagen antibodies were placed in the 96-well plate and allowed to react again for 15 minutes. After 15 minutes, a coloring stimulant was added to cause color development at room temperature for 15 minutes, and when 1M sulfuric acid was added again to stop the reaction (color development), the color of the reaction solution became yellow, and the degree of yellow color varied according to the progress of the reaction.

The absorbance of the yellowish 96-well plate was measured at 405 nm using an absorptiometer, and the expression level of collagenase was calculated by Calculation Equation 1 below. In particular, the reaction absorbance of the collected cell culture solution in the untreated group was taken as the absorbance of the control group.

Collagenase expression level (%)=A/B×100
A: Absorbance of the test substance-treated cell group
B: Absorbance of control group Meanwhile, the results of measuring the collagenase expression inhibitory effect of the test substances in the human fibroblasts are shown in Table 4 below as the degree of collagenase expression, which were compared to the degree of collagenase expression of the untreated group as 100.

TABLE 4

| | Concentration | Degree of Collagenase Expression (%) |
|---|---|---|
| Control (Untreated group) | | 100% |
| Positive control (Retinoic acid) | 5 μM | 75.0% |
| Ganoderma lucidum extract extracted using water (distilled water) | 50 ppm | 83.7% |
| Ganoderma lucidum extracts extracted using aqueous cyclodextrin solution in combination with ultrasonic extraction (1% β-CD aqueous solution * Ultrasonic Assisted extraction) | 1 ppm 10 ppm 50 ppm | 93.5% 82.7% 74.0% |

As shown in Table 4, the *Ganoderma lucidum* extracts extracted with the aqueous cyclodextrin solution according to the present disclosure effectively inhibited collagenase expression. In particular, the *Ganoderma lucidum* extracts showed higher collagenase expression inhibitory effect than the *Ganoderma lucidum* extract extracted with water without using the aqueous cyclodextrin solution.

From the results of Test Examples 1 and 2, it was confirmed that the *Ganoderma lucidum* extracts prepared according to the method for preparing an extract of the present disclosure contained a high concentration of the triterpenoid component. In addition, from the results of Test Examples 3 and 4, it was confirmed that the *Ganoderma lucidum* extracts prepared according to the present disclosure showed excellent MMP-1 and collagenase inhibitory effects. Accordingly, it can be seen that the *Ganoderma lucidum* extracts containing a high concentration of triterpenoids prepared according to the method for preparing an extract of the present disclosure have an anti-aging effect and thus can be used for reducing skin wrinkles and increasing skin elasticity.

The invention claimed is:

1. A method for preparing a *Ganoderma lucidum* extract, the method comprising extracting *Ganoderma lucidum* with an aqueous cyclodextrin solution to form a clathrate of a triterpenoid component of the *Ganoderma lucidum* and a cyclodextrin of the aqueous cyclodextrin solution,
   wherein the *Ganoderma lucidum* extract contains triterpenoids of *Ganoderma lucidum*, and
   wherein the aqueous cyclodextrin solution contains the cyclodextrin in a concentration ranging from 0.01 to 30% by weight based on total volume of the aqueous cyclodextrin solution.

2. The method of claim 1, further comprising an ultrasonic treatment during the extracting step of forming the clathrate of the cyclodextrin and the triterpenoid component of the *Ganoderma lucidum*.

3. The method of claim 1, wherein the cyclodextrin in the aqueous cyclodextrin solution is a mixture of α-cyclodextrin, β-cyclodextrin, and γ-cyclodextrin.

4. The method of claim 1, wherein the aqueous cyclodextrin solution comprises a mixture of βcyclodextrin and γ-cyclodextrin at a weight ratio of 1:1; or a mixture of α-cyclodextrin, β-cyclodextrin, and γ-cyclodextrin at a weight ratio of 1:1 to 2:0.5 to 2.

5. The method of claim 1, wherein temperature of the extraction is 15° C. to 100° C.

6. The method of claim 1, wherein duration of the extraction is 10 minutes to 24 hours.

7. The method of claim 2, wherein temperature of the extraction during the ultrasonic treatment is 15° C. to 35° C., and duration of the extraction is 10 minutes to 120 minutes.

* * * * *